United States Patent
Konya et al.

(10) Patent No.: US 11,110,193 B2
(45) Date of Patent: Sep. 7, 2021

(54) AROMA DIFFUSING DEVICE AND METHOD OF CONTROLLING AROMA DIFFUSING DEVICE

(71) Applicant: SONY CORPORATION, Tokyo (JP)

(72) Inventors: Satoshi Konya, Kanagawa (JP); Shuji Fujita, Tokyo (JP)

(73) Assignee: SONY CORPORATION, Tokyo (JP)

( * ) Notice: Subject to any disclaimer, the term of this patent is extended or adjusted under 35 U.S.C. 154(b) by 107 days.

(21) Appl. No.: 16/317,619

(22) PCT Filed: May 2, 2017

(86) PCT No.: PCT/JP2017/017225
§ 371 (c)(1),
(2) Date: Jan. 14, 2019

(87) PCT Pub. No.: WO2018/016153
PCT Pub. Date: Jan. 25, 2018

(65) Prior Publication Data
US 2019/0282720 A1    Sep. 19, 2019

(30) Foreign Application Priority Data

Jul. 21, 2016 (JP) .............................. JP2016-143634

(51) Int. Cl.
*A61L 9/12* (2006.01)
(52) U.S. Cl.
CPC .......... *A61L 9/122* (2013.01); *A61L 2209/11* (2013.01); *A61L 2209/12* (2013.01); *A61L 2209/133* (2013.01); *A61L 2209/134* (2013.01)
(58) Field of Classification Search
CPC .. A61L 9/122; A61L 2209/11; A61L 2209/12; A61L 2209/133; A61L 2209/134; A61L 9/12
(Continued)

(56) References Cited

U.S. PATENT DOCUMENTS

| 5,567,361 A | 10/1996 | Harper |
| 5,924,597 A | 7/1999 | Lynn |

(Continued)

FOREIGN PATENT DOCUMENTS

| EP | 0800832 | 10/1997 |
| JP | H02-220665 | 3/1990 |

(Continued)

OTHER PUBLICATIONS

International Search Report prepared by the Japan Patent Office dated Jun. 1, 2017, for International Application No. PCT/JP2017/017225.

(Continued)

*Primary Examiner* — Huy Tram Nguyen
(74) *Attorney, Agent, or Firm* — Sheridan Ross P.C.

(57) ABSTRACT

To provide an aroma diffusing device and a method of controlling an aroma diffusing device that can enable a plurality of functions to be achieved by operation inputs to one operation input part.

Provided is an aroma diffusing device including: a perfume holding part in which a perfume is held; an air blowing source configured to supply air to the perfume holding part; an aroma discharge part through which the air having passed through the perfume holding part is discharged; an operation input part on which an operation input for the air blowing source is performed by a user; and an air blowing source control part configured to control a supply state of the air on the basis of an operation input on the one operation input part.

20 Claims, 14 Drawing Sheets

(58) Field of Classification Search
USPC ........................................................ 422/124
See application file for complete search history.

(56) References Cited

U.S. PATENT DOCUMENTS

| | | | | |
|---|---|---|---|---|
| 6,404,168 | B1* | 6/2002 | Shoji | H01M 6/5033 307/66 |
| 7,962,017 | B2* | 6/2011 | Viera | A01M 1/2072 392/392 |
| 2002/0148911 | A1* | 10/2002 | Beck | A61H 33/60 239/310 |
| 2006/0039835 | A1* | 2/2006 | Nottingham | A61L 9/048 422/124 |
| 2007/0280653 | A1* | 12/2007 | Viera | A61L 9/122 392/395 |
| 2008/0299014 | A1* | 12/2008 | Kim | A61L 9/122 422/124 |
| 2011/0083757 | A1* | 4/2011 | Shore | F24F 1/0071 137/544 |
| 2014/0147484 | A1* | 5/2014 | Breuer | A61P 35/00 424/423 |
| 2014/0199206 | A1* | 7/2014 | Shen | F24F 11/77 422/3 |
| 2016/0000956 | A1* | 1/2016 | Jenkins | A61L 9/037 392/395 |
| 2016/0379506 | A1* | 12/2016 | Okada | G09B 19/00 434/236 |

FOREIGN PATENT DOCUMENTS

| | | |
|---|---|---|
| JP | H04-371160 | 12/1992 |
| JP | 2000-233018 | 8/2000 |
| JP | 2002-065832 | 3/2002 |
| JP | 2002-186660 | 7/2002 |
| JP | 2003-153997 | 5/2003 |
| JP | 2003-169585 | 6/2003 |
| JP | 2003-299720 | 10/2003 |
| JP | 2005-229700 | 8/2005 |
| JP | 2009-283368 | 12/2009 |
| JP | 2009-287470 | 12/2009 |
| JP | 2013-066522 | 4/2013 |
| JP | 2015-198825 | 11/2015 |
| WO | WO 2005/092400 | 10/2005 |

OTHER PUBLICATIONS

Extended European Seach Report for European Patent Application No. 17830673.4, dated Jul. 9, 2019, 9 pages.

* cited by examiner

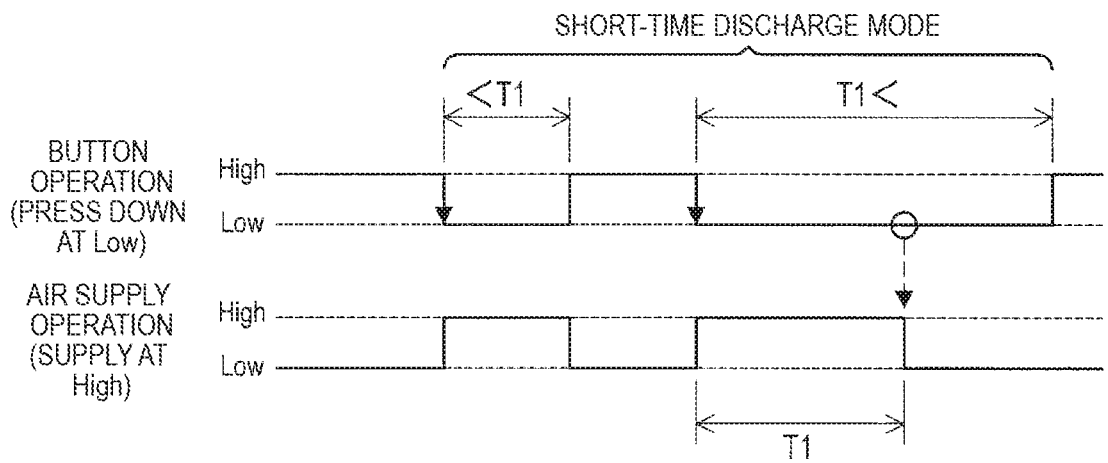
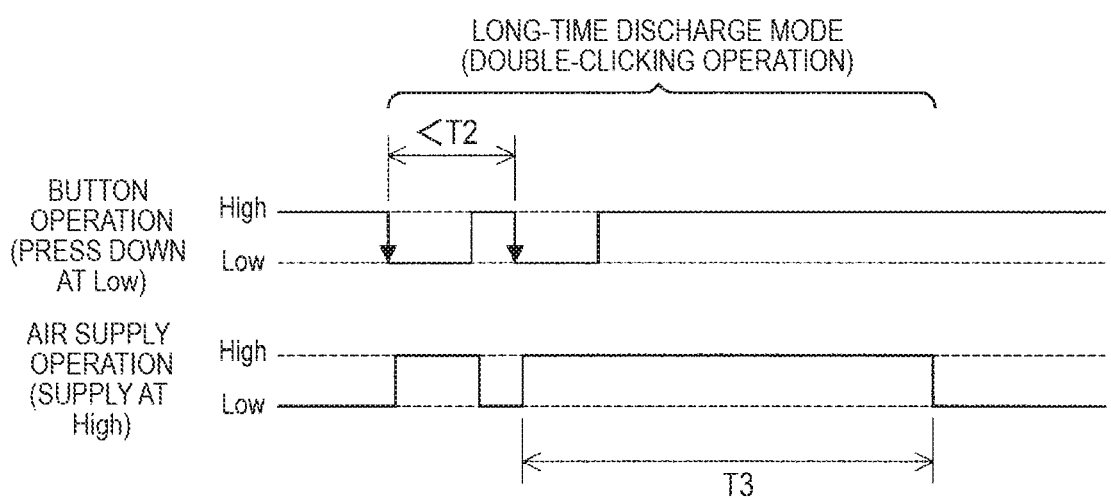

AROMA DIFFUSING DEVICE AND METHOD OF CONTROLLING AROMA DIFFUSING DEVICE

CROSS REFERENCE TO RELATED APPLICATIONS

This application is a national stage application under 35 U.S.C. 371 and claims the benefit of PCT Application No. PCT/JP2017/017225 having an international filing date of 2 May 2017, which designated the United States, which PCT application claimed the benefit of Japanese Patent Application No. 2016-143634 filed 21 Jul. 2016, the entire disclosures of each of which are incorporated herein by reference.

TECHNICAL FIELD

The present disclosure relates to an aroma diffusing device and a method of controlling an aroma diffusing device.

BACKGROUND ART

Conventionally, there are portable aroma diffusers. For example, Patent Literature 1 discloses a portable aroma diffuser that is easy to carry, can be used anywhere, and further allows a user to easily turn on/off diffusion of the fragrance so as to enjoy his/her favorite fragrance easily. In such an aroma diffuser, an aroma source, a blower fan, and a battery for driving the blower fan are stored in a housing, and when a part of the housing is opened, the blower fan is driven, and an air path for air from the blower fan to pass through the aroma source to be diffused to the outside of the housing is formed. When the part of the housing is closed, the air path from the aroma source to the outside of the housing is closed.

CITATION LIST

Patent Literature

Patent Literature 1: JP 2000-233018A

DISCLOSURE OF INVENTION

Technical Problem

In the aroma diffuser disclosed in Patent Literature 1, only on and off of the air blowing source can be switched by opening and closing the part of the housing or the like. In contrast to this, not only switching between on and off of the air blowing source, but if the operation state of the air blowing source can be switched, user convenience is improved more. In particular, if a plurality of functions can be achieved in an aroma diffuser by operation inputs to one operation input part, it is considered that operability and convenience are improved more.

Therefore, the present disclosure proposes an aroma diffusing device and a method of controlling an aroma diffusing device being novel and improved that can enable a plurality of functions to be achieved by operation inputs to one operation input part.

Solution to Problem

According to the present disclosure, there is provided an aroma diffusing device including: a perfume holding part in which a perfume is held; an air blowing source configured to supply air to the perfume holding part; an aroma discharge part through which the air having passed through the perfume holding part is discharged; an operation input part on which an operation input for the air blowing source is performed by a user; and an air blowing source control part configured to control a supply state of the air on the basis of an operation input on the one operation input part.

In addition, according to the present disclosure, there is provided a method of controlling an aroma diffusing device, the method including: accepting an operation input on one operation input part made by a user; and activating an air blowing source when the operation input is accepted to pass air through a perfume holding part in which a perfume is held and discharge an aroma. A supply state of the air is controlled on the basis of the operation input on the one operation input part.

Advantageous Effects of Invention

According to the present disclosure as described above, it is possible to enable a plurality of functions to be achieved by operation inputs to one operation input part.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 7 is an explanatory diagram for describing a short-time discharge mode.

FIG. 8 is an explanatory diagram for describing a long-time discharge mode.

MODE(S) FOR CARRYING OUT THE INVENTION

Figure 1:
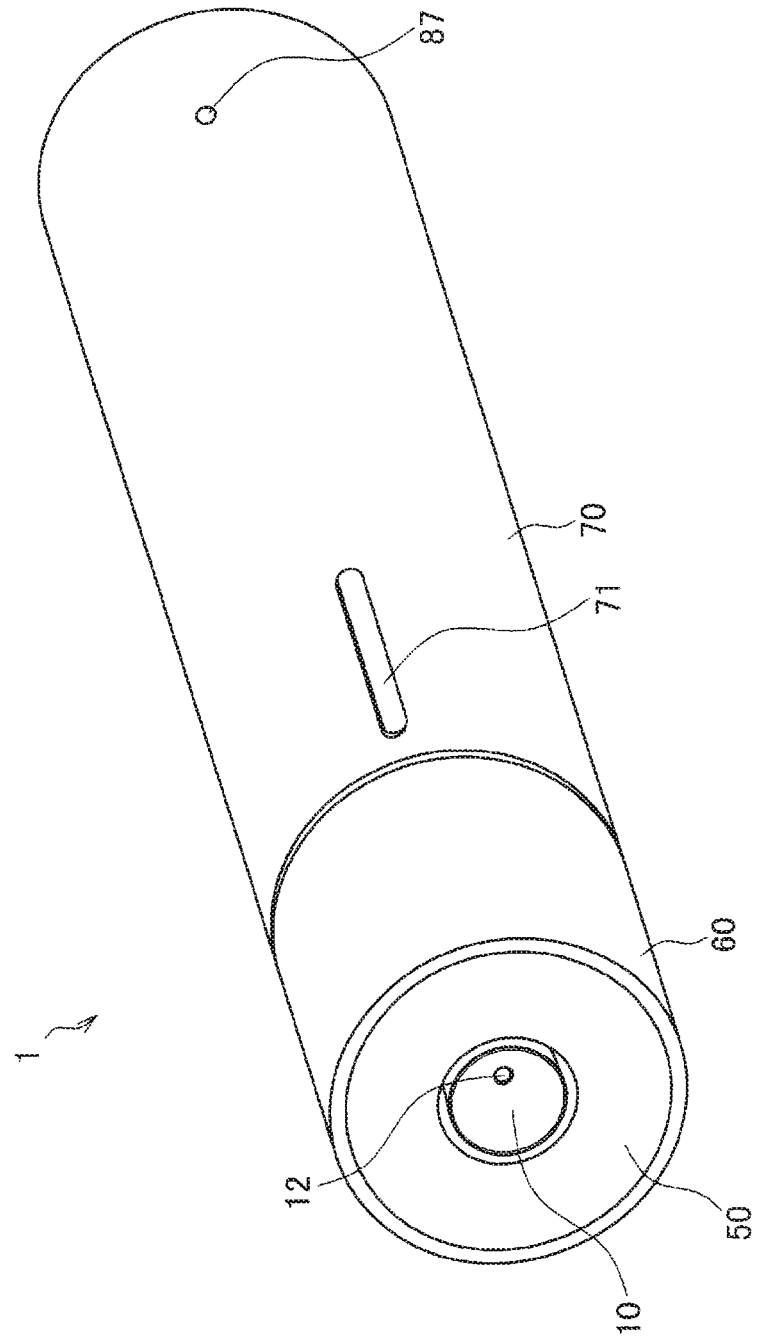
FIG. 1 is a perspective view showing an example of an aroma diffusing device according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. First embodiment (example of controlling discharge time)
1-1. Overall configuration example of aroma diffusing device
1-2. Configuration example of control system
1-3. Method of controlling aroma diffusing device
2. Second embodiment (example of controlling discharge amount per unit time)
2-1. Configuration example of control system
2-2. Variation

1. First Embodiment (1-1. Overall Configuration Example of Aroma Diffusing Device)

Figure 2:
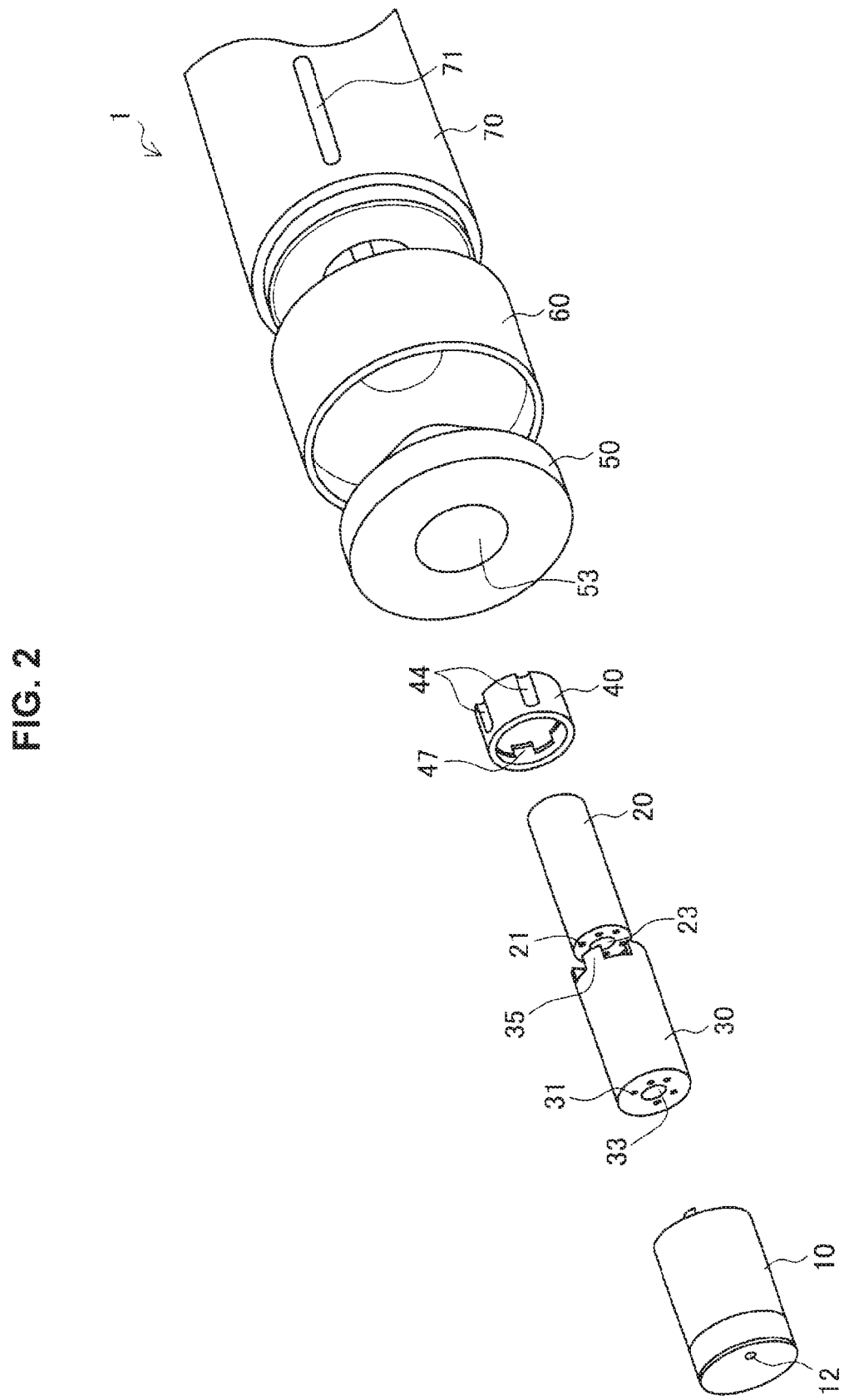
FIG. 2 is an exploded perspective view of the aroma diffusing device according to the embodiment.
Figure 3:
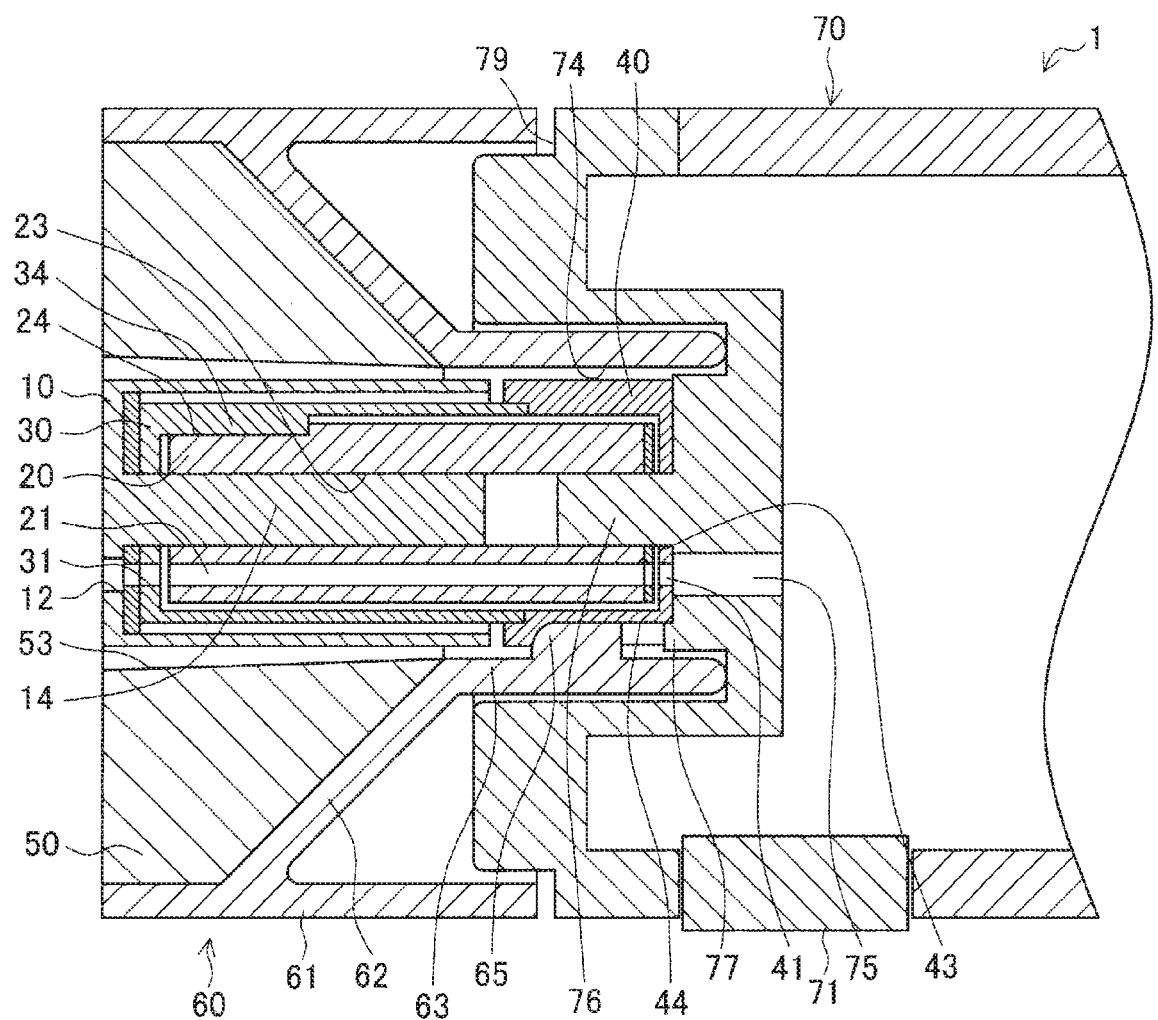
FIG. 3 is an axial sectional view of the aroma diffusing device according to the embodiment.

First, with reference to FIG. 1 to FIG. 3, an example of an aroma diffusing device 1 according to a first embodiment of the present disclosure will be described. FIG. 1 is a perspective view showing the aroma diffusing device 1 according to the present embodiment, FIG. 2 is an exploded perspective view of the aroma diffusing device 1, and FIG. 3 is an axial sectional view of the aroma diffusing device 1. Note that, in the following description, the direction in which a perfume holding part (perfume cartridge) 20 in the aroma diffusing device 1 is arranged will be called the front side, and the direction in which a base part 70 is arranged will be called the back side.

The aroma diffusing device 1 according to the present embodiment is the portable aroma diffusing device 1 that can be freely carried by a user. Such an aroma diffusing device 1 includes an upper cover 10, the perfume cartridge 20 as a perfume holding part, a cartridge case 30, a lower cover 40, a prism part 50, a rotating operation part 60, and the base part 70. Such an aroma diffusing device 1 is a device that flows air to a desired air flow path 21 selected by the user from among a plurality of air flow paths 21 provided for the perfume cartridge 20, and emits an aroma held on the inner peripheral surface of each of the air flow paths 21 while vaporizing the aroma. For example, in the aroma diffusing device 1, by causing air supplied from an air pump not shown as an air blowing source to pass through the air flow paths 21 of the perfume cartridge 20, the aroma in the wet state is vaporized, and flows out of the air flow paths 21 with air.

Such an aroma diffusing device 1 may be used as a device that emits a fragrance to a limited range, for example. For example, the aroma diffusing device 1 may be used by the user causing the fragrance to be emitted one or more times close to his/her own face so as to feel relaxed. In this case, since the aroma diffusing device 1 according to the present embodiment does not diffuse the fragrance to a wide range, it is possible to make the fragrance unlikely to be sensed by surrounding people.

The cartridge case 30 has a cylindrical outer shape whose end at the back side, of both ends in the axial direction, is open. The cartridge case 30 holds the perfume cartridge 20 inside. The cartridge case 30 has a circular opening 33 centering on the axis center in the front side end surface. In addition, the cartridge case 30 has holes 31 around the opening 33 that communicate with the air flow paths 21 of the perfume cartridge 20, respectively.

A locking protrusion 34 extending in the axial direction is provided on the inner peripheral surface of the cartridge case 30 (see FIG. 3). Such a locking protrusion 34 engages with a locking groove 24 provided in the outer peripheral surface of the perfume cartridge 20 when the perfume cartridge 20 is inserted into the cartridge case 30 (see FIG. 3). Accordingly, the perfume cartridge 20 and the cartridge case 30 are positioned, and the air flow paths 21 and the holes 31 communicate. The locking protrusion may be provided for the cartridge case 30, and the locking groove may be provided for the perfume cartridge 20.

In addition, the cartridge case 30 has a plurality of claw portions 35 on the back side end (see FIG. 2). The claw portions 35 are formed at regular intervals by partly extending the position of the back side end of the cartridge case 30 in the axial direction.

The perfume cartridge 20 has a cylindrical shape. The perfume cartridge 20 is provided with the plurality of air flow paths 21 through which air supplied from the air pump which is an example of an air blowing source passes. In the air flow paths 21, the aroma is held in the wet state. The aroma is held in a state adhering to the inner peripheral surface of the air flow paths 21. The aroma may be, for example, essential oil, essential oil diluted with ethanol, or the like. There may be one air flow path 21 or a plurality of air flow paths 21. In the aroma diffusing device 1 according to the present embodiment, the perfume cartridge 20 having five air flow paths 21 is used.

The lower cover 40 has a cylindrical outer shape whose end at the front side, of both ends in the axial direction, is open. The lower cover 40 holds the back side of the cartridge case 30. The lower cover 40 has a circular opening 43 centering on the axis center in the back side end surface (see FIG. 3). In addition, the lower cover 40 has holes 41 around the opening 43 that communicate with the air flow paths 21 of the perfume cartridge 20, respectively (see FIG. 3).

The back end of the cartridge case 30 is inserted into the front side opening of the lower cover 40. The lower cover 40 has, in the inner peripheral surface, a plurality of accepting recesses 47 in which the claw portions 35 of the cartridge case 30 are arranged. The number of the accepting recesses 47 corresponds to the number of the claw portions 35. The number of the claw portions 35 and the accepting recesses 47 agrees with the number of the air flow paths 21 of the perfume cartridge 20. Accordingly, by causing the lower cover 40 to hold the cartridge case 30 that is holding the perfume cartridge 20 in any rotating phase, the plurality of air flow paths 21 communicate with the holes 41 of the lower cover 40.

The upper cover 10 is mounted on the outer side of the cartridge case 30. The upper cover 10 has a cylindrical outer shape whose end at the back side, of both ends in the axial direction, is open. The upper cover 10 has an aroma discharge part 12 in the front side end surface that may communicate with any one of the plurality of air flow paths 21 of the perfume cartridge 20. Air including an aromatic component having passed through any of the air flow paths 21 of the perfume cartridge 20 and having been vaporized is discharged to the outside via the aroma discharge part 12. The inner diameter of the aroma discharge part 12 is not particularly limited, but in order not to interfere with the flow of air that flows through the air flow paths 21 of the perfume cartridge 20, the inner diameter of the aroma discharge part 12 may be at least more than or equal to the inner diameter of the air flow paths 21.

The upper cover 10 includes a fixed shaft 14 extending in the axial direction from the inner side surface of the front side end surface (see FIG. 3). The fixed shaft 14 is inserted in the opening 33 of the cartridge case 30 and an axial hole 23 of the perfume cartridge 20. The upper cover 10 is capable of rotating relatively with respect to the cartridge case 30 that holds the perfume cartridge 20 using the fixed shaft 14 as a rotation axis, and the air flow paths 21 communicating with the aroma discharge part 12 are switched according to a relative position. At the leading end of the fixed shaft 14, an engaging part not shown including a half body cut along the axis center is provided. Such an engaging part should only have a shape that is fitted over a fixed shaft 76 of the base part 70 and is attachable/detachable, and is not limited to the above-described shape (see FIG. 3).

In the aroma diffusing device 1 according to the present embodiment, it is possible for the user to exchange an assembly obtained by integrating the upper cover 10, the cartridge case 30, the perfume cartridge 20, and the lower cover 40. Such an assembly may have a single-use perfume cartridge 20, or may have a recycle-type perfume cartridge 20 that can be charged with an aroma again.

The rotating operation part 60 is arranged on the further outer peripheral side relative to the upper cover 10, the cartridge case 30, the perfume cartridge 20, and the lower cover 40. The rotating operation part 60 has an outer peripheral tube part 61, a cone part 62, and an inner peripheral tube part 63. The inner peripheral tube part 63 has a locking protrusion 65 on the inner peripheral surface. The outer peripheral tube part 61 and the inner peripheral tube part 63 are connected with the intervention of the cone part 62. The large-diameter-side end of the cone part 62 is connected to the axial central part of the inner peripheral surface of the outer peripheral tube part 61. In addition, the small-diameter-side end of the cone part 62 is connected to the front side end of the inner peripheral tube part 63. The prism part 50 is arranged in a space at the front side of the cone part 62. The prism part 50 has an axial hole 53 centering on the axis center. In the axial hole 53, the upper cover 10, the cartridge case 30, and the perfume cartridge 20 are arranged.

The upper cover 10, the cartridge case 30, the perfume cartridge 20, and the lower cover 40 are inserted into the inside of the inner peripheral tube part 63 of the rotating operation part 60. At this time, the locking protrusion 65 of the inner peripheral tube part 63 is arranged in any of a plurality of locking grooves 44 provided in the outer peripheral surface of the lower cover 40. Accordingly, the lower cover 40 as well as the cartridge case 30 and the perfume cartridge 20 held by the lower cover 40 can rotate integrally with the rotating operation part 60. In addition, since the upper cover 10 is capable of rotating relatively with respect to the cartridge case 30, the perfume cartridge 20, and the lower cover 40, the rotating operation part 60 and the upper cover 10 are also capable of rotating relatively.

The rotating operation part 60, the upper cover 10, the perfume cartridge 20, the cartridge case 30, the lower cover 40, and the like are supported by the base part 70. The base part 70 has a recess 74 having a circular cross section at the central part of the front side surface. The inner peripheral tube part 63 of the rotating operation part 60 is inserted into such a recess 74. In addition, the base part 70 has an annular level difference part 79 at the outer edge of the front side surface. The outer peripheral tube part 61 of the rotating operation part 60 is arranged at such a level difference part 79. That is, the outer peripheral tube part 61 is arranged at the level difference part 79, the inner peripheral tube part 63 of the rotating operation part 60 is arranged in the recess 74, and further, the lower cover 40, the perfume cartridge 20, and the like are arranged on the inner side of the inner peripheral tube part 63.

The base part 70 has the fixed shaft 76 standing erect on the bottom surface of the recess 74 and extending toward the front side. The fixed shaft 76 is inserted through the opening 43 of the lower cover 40 and the axial hole 23 of the perfume cartridge 20. For example, the fixed shaft 76 is lightly press-fitted into the axial hole 23 of the perfume cartridge 20, and accordingly, the rotating operation part 60, the upper cover 10, the perfume cartridge 20, the cartridge case 30, the lower cover 40, and the like are supported by the base part 70.

An engaging part not shown including a half body cut along the axis center is provided at the leading end of the fixed shaft 76. The engaging part of the fixed shaft 76 is fitted into the axial hole 23 of the perfume cartridge 20 in an axially 180° rotated state with respect to the engaging part at the leading end of the fixed shaft 14 of the upper cover 10. Accordingly, a relative rotation of the upper cover 10 and the base part 70 cannot be made. Therefore, the rotating operation part 60, the perfume cartridge 20, the cartridge case 30, and the lower cover 40 are capable of rotating relatively with respect to the base part 70. However, similarly to the engaging part of the upper cover 10, the engaging part should only have a shape that is fitted in the fixed shaft 14 of the upper cover 10 and is attachable/detachable, and is not limited to the above-described shape.

The base part 70 has an air supply port 75 in the bottom surface of the recess 74. In addition, a protrusion 77 for positioning is provided on the bottom surface of the recess 74. Such a protrusion 77 is locked in the locking groove 44 of the lower cover 40 in which the locking protrusion 65 of the rotating operation part 60 is arranged. In the outer peripheral surface of the lower cover 40, the plurality of locking grooves 44 are provided at regular intervals in correspondence to the position of the air flow paths 21 of the perfume cartridge 20. Any of the air flow paths 21 communicates with the air supply port 75 in the state where the protrusion 77 is locked in any of the locking grooves 44. Therefore, by rotating the rotating operation part 60, the air flow path 21 that communicates with the air supply port 75 is switched.

Such a protrusion 77 may be formed as a separate member from the base part 70, and may be urged by a spring or the like to the lower cover 40 side. That is, the protrusion 77 may be retracted by contraction of the spring or the like while the perfume cartridge 20 is being rotated, and when any of the locking grooves 44 agrees with the position of the protrusion 77, the protrusion 77 may protrude to the locking groove 44 side. Accordingly, the lower cover 40, the rotating operation part 60, and the like can be rotated without changing the distance between the base part 70 and the lower cover 40 or the like.

Inside the base part 70, an air pump, a battery, a circuit board, and the like, neither shown, are provided. The air pump is a mode of the air blowing source, and is driven by electric power supplied from the battery to introduce air to the air supply port 75. The air pump may be, for example, a diaphragm type pump that deforms a diaphragm by supplying an AC current to a piezoelectric element to suck and pump air. However, the air blowing source is not limited to the air pump, but may be, for example, a blower of the type that rotates a fan. The battery may be a replaceable battery from which only discharge is performed, or may be a rechargeable secondary battery. In the aroma diffusing device 1 according to the present embodiment, a secondary battery is used as the battery. For example, a USB terminal or the like for charging the secondary battery is provided in the back side end surface of the aroma diffusing device 1.

A control circuit for performing driving control of the air pump, a driving circuit for driving the air pump, and the like are mounted on the circuit board. Switching of the driven state of the air pump is performed by operating an operation button 71 as the operation input part. By pressing such an operation button 71, on and off of a switch not shown are switched. Instead of the operation button 71, a touch sensor type operation input part may be provided. The control circuit generates a control signal for the air pump on the basis of on/off of the switch by an operation input on the operation button 71 made by the user to control the driven state of the air pump. When electric power is supplied to the air pump by driving control performed by the control circuit, the air pump supplies air to the perfume cartridge 20 via the air supply port 75.

In addition, in the aroma diffusing device 1 according to the present embodiment, a light source such as a light emitting diode (LED) is mounted on the circuit board. Such a light source indicates the operation state of the aroma diffusing device 1, and is controlled by the control circuit mounted on the circuit board. Light output from the light source is visible from the outside through a hole 87 provided in the outer peripheral surface of the base part 70. A method of controlling the air pump and a method of controlling the light source will be described later in detail.

Figure 4:
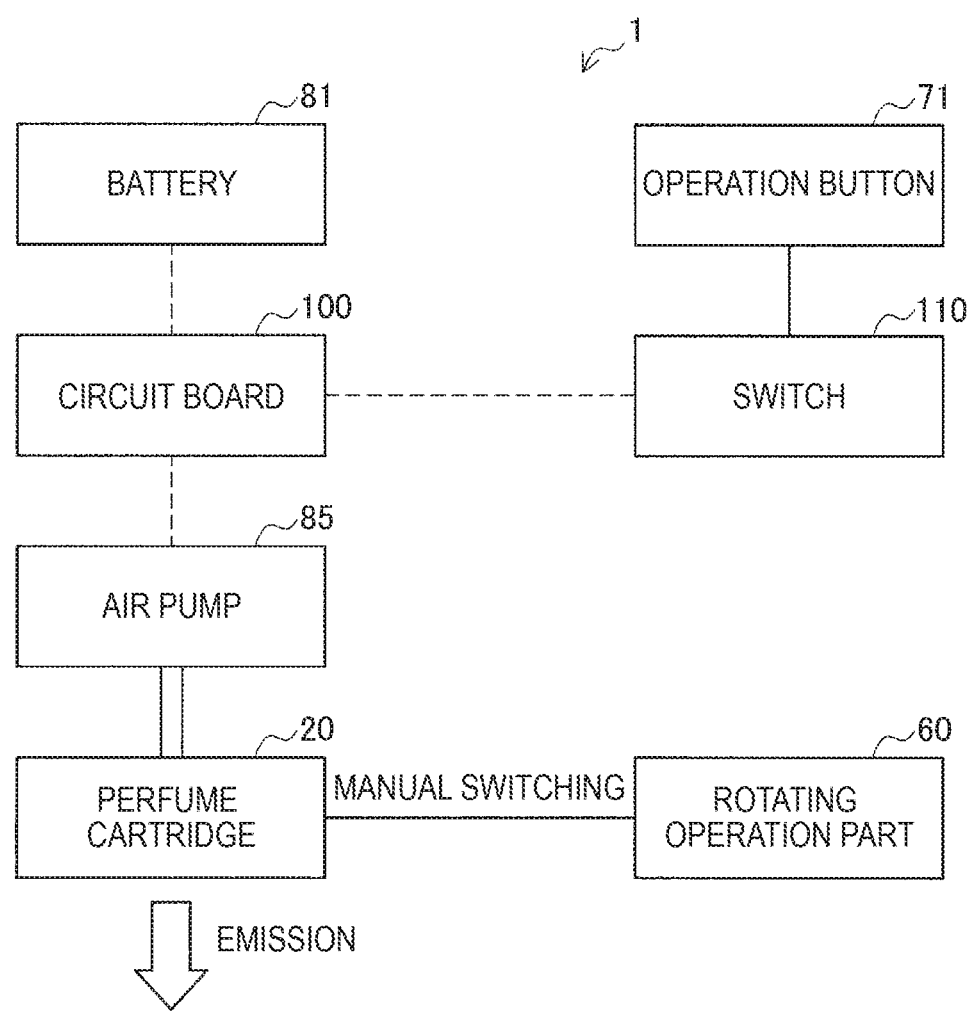
FIG. 4 is a block diagram showing a configuration example of the aroma diffusing device according to the embodiment.

FIG. 4 is a block diagram schematically showing a configuration of the aroma diffusing device 1. A battery 81 and an air pump 85 are electrically connected with the intervention of the circuit board 100. On and off of a switch 110 are switched by the operation button 71. Such a switch 110 is a self-reset type momentary switch brought into an on state while the operation button 71 is being pressed down, and brought into an off state when pressing down of the operation button 71 is suspended. The control circuit on the circuit board 100 outputs a driving signal to the driving circuit for the air pump 85 on the basis of an operation input on the operation button 71. Accordingly, the air pump 85 is driven in a predetermined driven state, and supplies air to the perfume cartridge 20.

The perfume cartridge 20 rotates along with a rotation of the rotating operation part 60 caused by the user, and accordingly, the air flow path 21 to which air may be supplied is switched. Air supplied to the perfume cartridge 20 passes through the air flow path 21 while evaporating the aroma held on the inner surface of the air flow path 21 selected by the user, and is discharged to the outside from the aroma discharge part 12. Accordingly, a desired aroma is discharged.

(1-2. Configuration Example of Control System)

Next, a configuration example of a control system that performs driving control of the air pump 85 of the aroma diffusing device 1 according to the present embodiment will be described.

Figure 5:
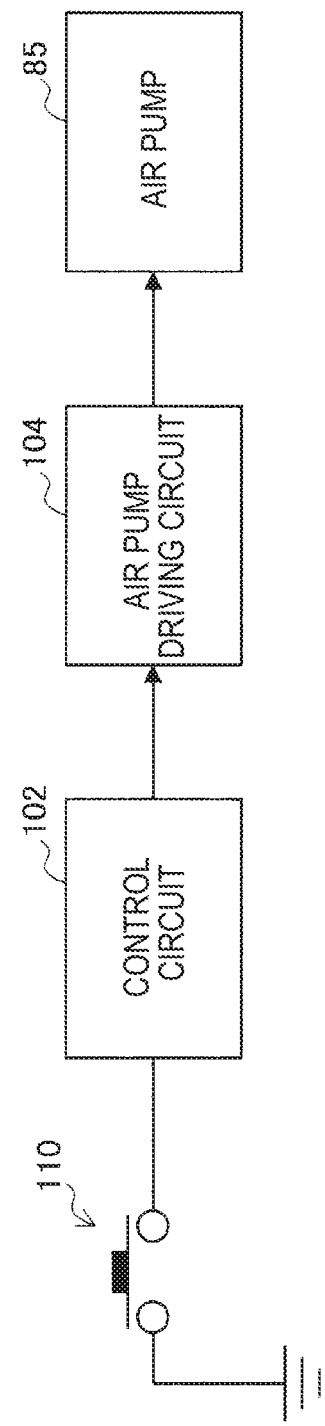
FIG. 5 is a block diagram showing an example of a system configuration of the aroma diffusing device according to the embodiment.

FIG. 5 is a block diagram showing a basic configuration of a control system for the air pump 85. Such a control system has the switch 110, a control circuit 102, and an air pump driving circuit 104. The switch 110 is the momentary type switch 110, on and off of which are switched by the operation button 71. Such a switch 110 is connected to the control circuit 102. The control circuit 102 generates a driving signal for the air pump 85 on the basis of on/off of the switch 110, and outputs the driving signal to the air pump driving circuit 104. That is, in the aroma diffusing device 1 according to the present embodiment, the control circuit 102 is equivalent to an air blowing source control part. The air pump driving circuit 104 controls electric power supplied to the air pump 85 on the basis of the driving signal. Accordingly, the air pump 85 is driven in a predetermined operation state to supply air to the perfume cartridge 20.

Such a control circuit 102 includes a timer for counting a predetermined elapsed time. The control circuit 102 is configured using a field-programmable gate array (FPGA), for example, and may be configured at lower cost than in the case of using a microcomputer such as a central processing unit (CPU).

Note that the basic configuration of the control system, shown in FIG. 5 may be applied as a control system for the aroma diffusing device 1 according to a second embodiment which will be described later.

Figure 6:
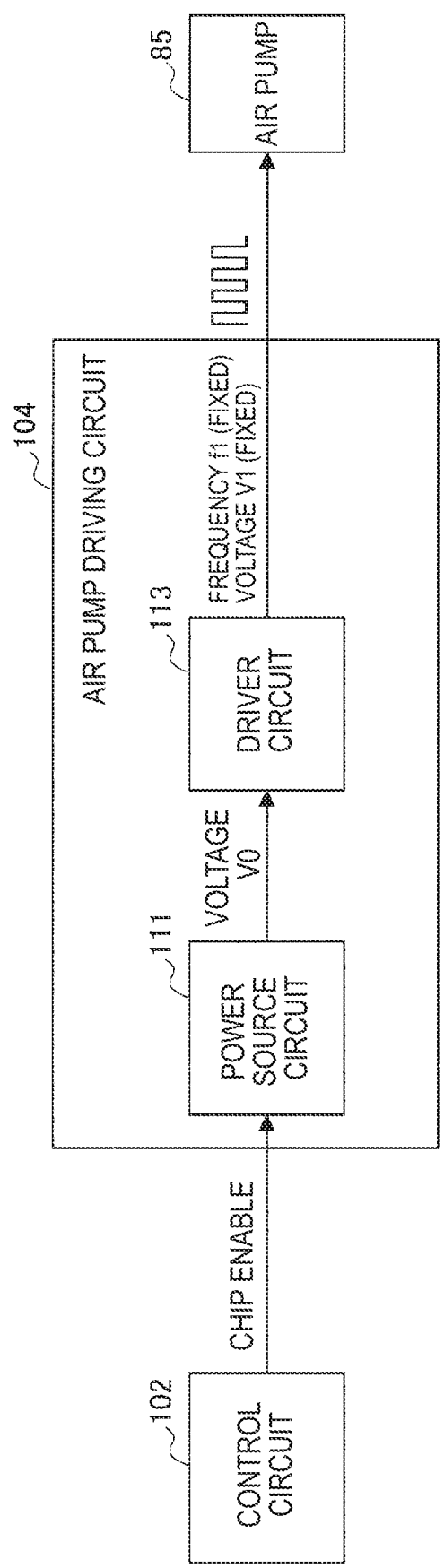
FIG. 6 is a block diagram showing a specific example of a system configuration of the aroma diffusing device according to the embodiment.

FIG. 6 is an explanatory diagram specifically showing a configuration of the control system for the aroma diffusing device 1 according to the present embodiment. In the example shown in FIG. 6, the air pump driving circuit 104 includes a power source circuit 111 and a driver circuit 113. In addition, the driver circuit 113 has a booster not shown that amplifies the voltage. The booster may be a DCDC converter, for example.

The control circuit 102 generates a chip enable signal on the basis of the on/off state of the switch 110, and outputs the chip enable signal to the power source circuit 111 of the air pump driving circuit 104. The power source circuit 111 supplies electric power of a voltage V0 set in advance to the driver circuit 113 while the chip enable signal is being input. The driver circuit 113 outputs a voltage signal of a voltage V1 generated by amplifying the voltage V0 to the air pump 85 at a frequency f1 set in advance while electric power is being supplied. The air pump 85 is a diaphragm type pump through use of a piezoelectric element, and performs an air discharge operation in accordance with the frequency f1 of the voltage signal. Accordingly, the air pump 85 supplies a constant flow rate of air to the perfume cartridge 20 while the voltage signal is being input.

Here, in the aroma diffusing device 1 according to the first embodiment, the time of air supply from the air pump 85 is controlled and the time of aroma discharge is controlled on the basis of operation inputs on one operation button 71. Accordingly, a plurality of discharge functions are achieved. Specifically, in the aroma diffusing device 1 according to the present embodiment, the control circuit 102 controls the time of generating the chip enable signal on the basis of the on/off state of the switch 110 switched by the operation button 71. Accordingly, the time of air supply supplied to the perfume cartridge 20 is controlled on the basis of an operation input on the operation button 71. In the aroma diffusing device 1 according to the present embodiment, a short-time discharge mode and a long-time discharge mode can be selected as aroma discharge modes controlled on the basis of an operation input on one operation button 71.

FIG. 7 to FIG. 10 are explanatory diagrams for describing aroma discharge modes switched in accordance with the pressed state of the operation button 71. FIG. 7 is an explanatory diagram of the short-time discharge mode, and FIG. 8 is an explanatory diagram of the long-time discharge mode. FIG. 7 to FIG. 10 each show the operation state of the operation button 71 (the on/off state of the switch 110) and the state of an air supply operation performed by the air pump 85. In the operation state of the operation button 71, the "Low" state indicates a state in which the operation button 71 is being pressed down. In addition, in the air supply operation state, the "High" state indicates a state in which air is being supplied.

In either mode of the short-time discharge mode and the long-time discharge mode, basically, when the operation button 71 is pressed down so that the switch 110 is switched from off to on, air supply by the air pump 85 is started, and aroma discharge is started. On the other hand, after air supply by the air pump 85 is started, air supply is stopped at predetermined timing in accordance with timing when the switch 110 is switched from on to off, a duration of the on state of the switch 110, a time interval when an operation of switching the switch 110 from off to on is repeated, or the like.

The aroma discharge operation in the short-time discharge mode is performed by continuously pressing down the operation button 71 for a desired time. As shown in FIG. 7, in the short-time discharge mode, air supply is started when the operation button 71 is pressed down so that the switch 110 is turned on. Then, air supply is stopped when the switch 110 is turned off unless an elapsed time T since the switch 110 is turned on exceeds a first threshold value T1 set in advance. On the other hand, in such a short-time discharge mode, when the elapsed time T since the switch 110 is turned on exceeds the first threshold value T1, air supply is stopped at that point of time.

Therefore, even in the case where the operation button 71 is continuously pressed down without user intention while he/she is carrying the aroma diffusing device 1 in a bag, for example, aroma discharge is stopped midway. Accordingly, reduction in remaining capacity of the battery 81 is suppressed, and it is possible to allow the perfume cartridge 20 to last a long time. The first threshold value T1 which is the maximum continuous discharge time in the short-time discharge mode may be set at an appropriate value. For example, the first threshold value T1 may be set at 5 to 10 seconds.

In addition, the aroma discharge operation in the long-time discharge mode is performed by double-clicking the operation button 71. As shown in FIG. 8, in the long-time discharge mode, air supply is started when the switch 110 is switched from off to on by a first operation input in which the operation button 71 is pressed down. In addition, when the first operation input is released once to return the switch 110 to the off state, and then the switch 110 is switched from off to on by a second operation input, air supply is started again. At this time, in the case where the second operation input is started before the elapsed time (time interval) T since the first operation input is started exceeds a second threshold value T2, air supply is stopped when the elapsed time T since air supply is started by the second operation input exceeds a third threshold value T3.

Therefore, in the case where the user wishes to cause an aroma to be discharged for a long time in advance, for example, by performing a double-clicking operation, it is possible to cause the aroma to be continuously discharged thereafter in the state where pressing down of the operation button 71 is released. The second threshold value T2 for starting aroma discharge in the long-time discharge mode may be set at an appropriate value. For example, the second threshold value T2 may be set at 0.5 to 1 second. In addition, the third threshold value T3 which is the aroma discharge time in the long-time discharge mode may also be set at an appropriate value. For example, the third threshold value T3 may be set at 10 to 30 seconds.

Figure 9:
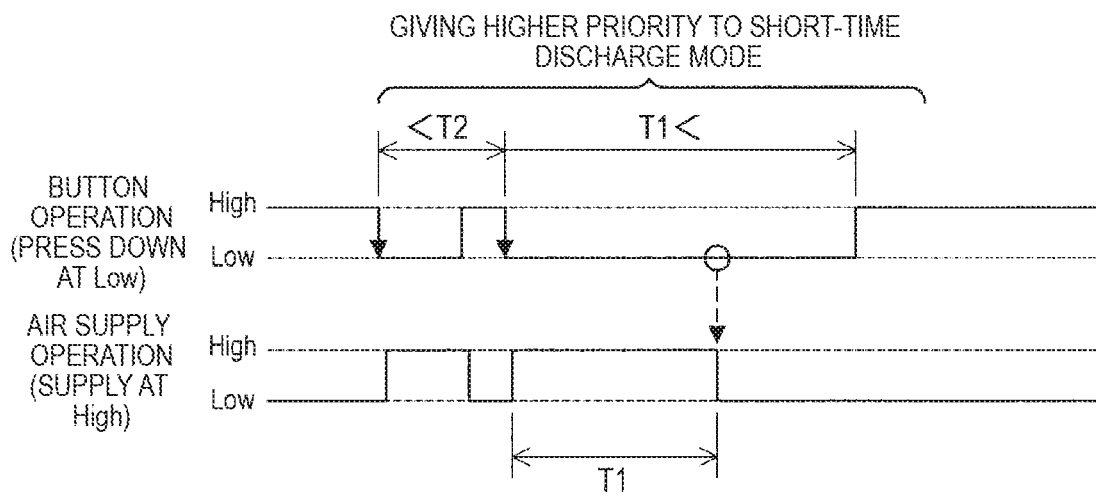
FIG. 9 is an explanatory diagram for describing an example in which a higher priority is given to the short-time discharge mode.

In addition, in the aroma diffusing device 1 according to the present embodiment, it is set such that a higher priority is given to the short-time discharge mode than the long-time discharge mode. As shown in FIG. 9, even in the case where the second operation input is started before the elapsed time T since the first operation input is started exceeds the second threshold value T2, when the elapsed time (time interval) T in which the switch 110 is maintained in the on state since the switch 110 is turned on by the second operation input exceeds the above-described first threshold value T1, air supply is stopped at that point of time.

Therefore, in the case where, when performing the operation for the short-time discharge mode, the user once presses down the operation button 71, and then releases the operation button 71 by an erroneous operation, and further continuously presses down the operation button 71 again, the air supply operation in the short-time discharge mode is performed. Accordingly, it is possible to prevent aroma discharge in the long-time discharge mode from being performed in the case where the user wishes aroma discharge in the short-time discharge mode.

Figure 10:
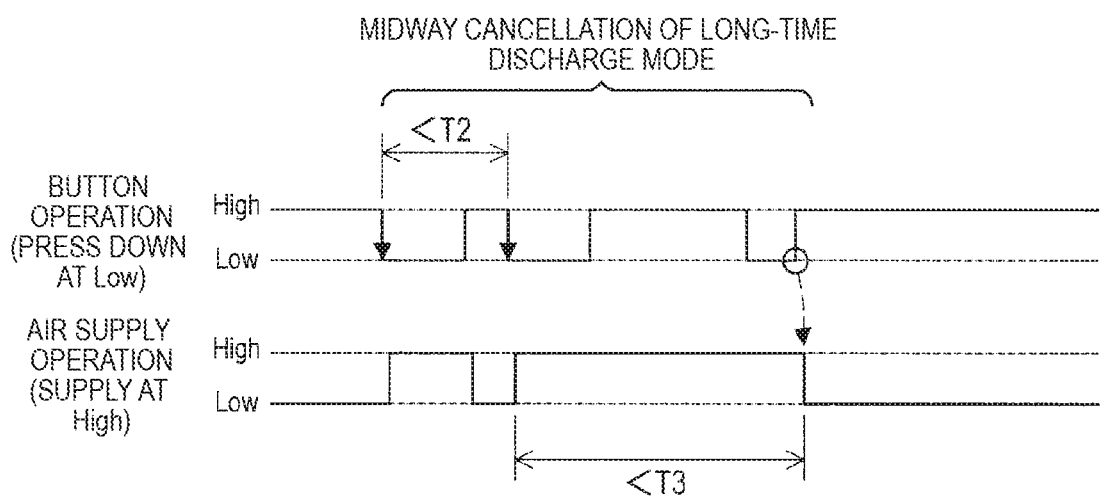
FIG. 10 is an explanatory diagram for describing an example in which the long-time discharge mode is cancelled midway.

In addition, in the aroma diffusing device 1 according to the present embodiment, even in the case where aroma discharge in the long-time discharge mode operation is started, the discharge operation can be released midway. As shown in FIG. 10, even in the case where the aroma discharge operation in the long-time discharge mode operation is started by a double-clicking operation on the operation button 71, air supply is stopped with a third operation input is performed again for a short time, as described with reference to FIG. 8. That is, when turning on/off of the switch 110 by the third operation input is performed before the elapsed time T since air supply is started by the second operation input exceeds the third threshold value T3, air supply is stopped immediately when the switch 110 is turned off.

Therefore, it is possible for the user to sop the aroma discharge operation in the long-time discharge mode with his/her own intention, so that reduction in remaining capacity of the battery 81 is prevented, and it is possible to allow the perfume cartridge 20 to last a long time.

Further, in the aroma diffusing device 1 according to the present embodiment, in the case where the remaining capacity of the battery 81 has decreased, the control circuit 102 may exert control of causing the user to recognize the reduction in remaining capacity of the battery 81 when the operation button 71 is pressed down so that the switch 110 is switched to on. For example, the control circuit 102 may light up the light source for a predetermined time when the operation button 71 is pressed down so that the switch 110 is switched to on. Accordingly, it is possible to cause the user to recognize the reduction in remaining capacity of the battery 81 and prompt for charging of the battery 81. For example, the control circuit 102 may light up the light source when the operation button 71 is pressed down in the case where the output voltage of the battery 81 is less than 10% of a rated voltage. The light up time of the light source on that occasion may be set at an appropriate time. For example, the light up time of the light source may be set at 1 to 5 seconds. In addition, the control circuit 102 may vary the number of lighting up the light source, light up interval, light up time, or the like in accordance with the remaining capacity of the battery 81.

Besides, the control circuit 102 may light up the light source on the basis of the operation state of the aroma diffusing device 1. On that occasion, the control circuit 102 may change the color of the light source to be lit up on the basis of the operation state of the aroma diffusing device 1. For example, when charging the battery 81, the control circuit 102 may light up the light source for a while until charging is completed, that is, for a while until the remaining capacity of the battery 81 exceeds the rated voltage. On that occasion, the control circuit 102 may light up the light source in a color different from the light up color of the light source when informing a reduction in remaining capacity of the battery 81. Note that, in the case where the control circuit 102 exerts control over the light source, the control circuit 102 is equivalent to a display control part.

In this manner, in the aroma diffusing device 1 according to the present embodiment, the aroma discharge modes illustrated in FIG. 7 to FIG. 10 are controlled on the basis of operation inputs on one operation button 71. Thus, the number of operation buttons is minimized, and the circuit configuration is simplified. Therefore, the aroma diffusing device 1 can be reduced in size, and the manufacturing cost can be suppressed. In addition, since the aroma diffusing device 1 according to the present embodiment can switch the aroma discharge mode by an operation input on one operation button 71, user operability and convenience are increased.

(1-3. Method of Controlling Aroma Diffusing Device)

Figure 11:
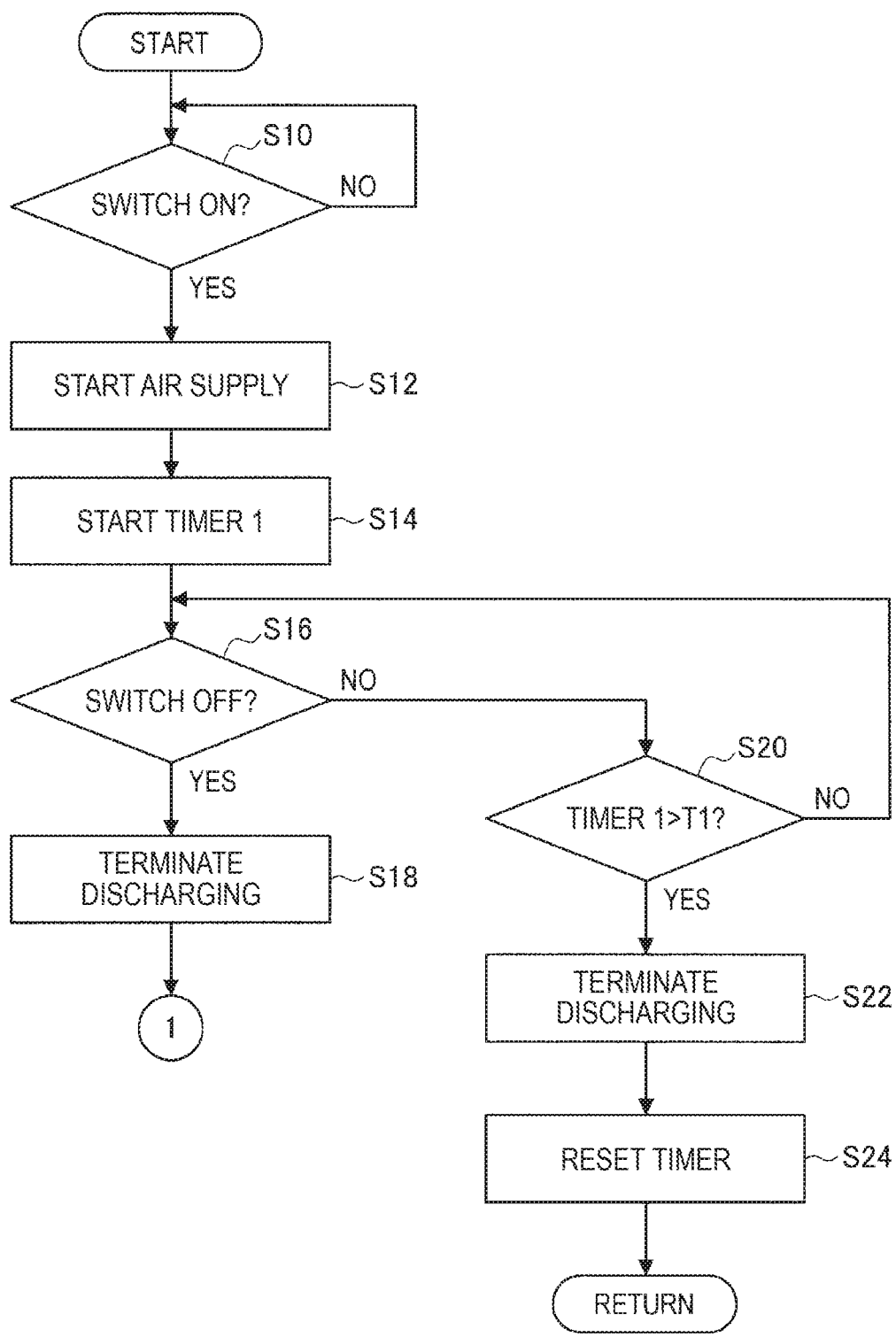
FIG. 11 is a flowchart for describing a flow of a method of controlling the aroma diffusing device according to the embodiment.
Figure 12:
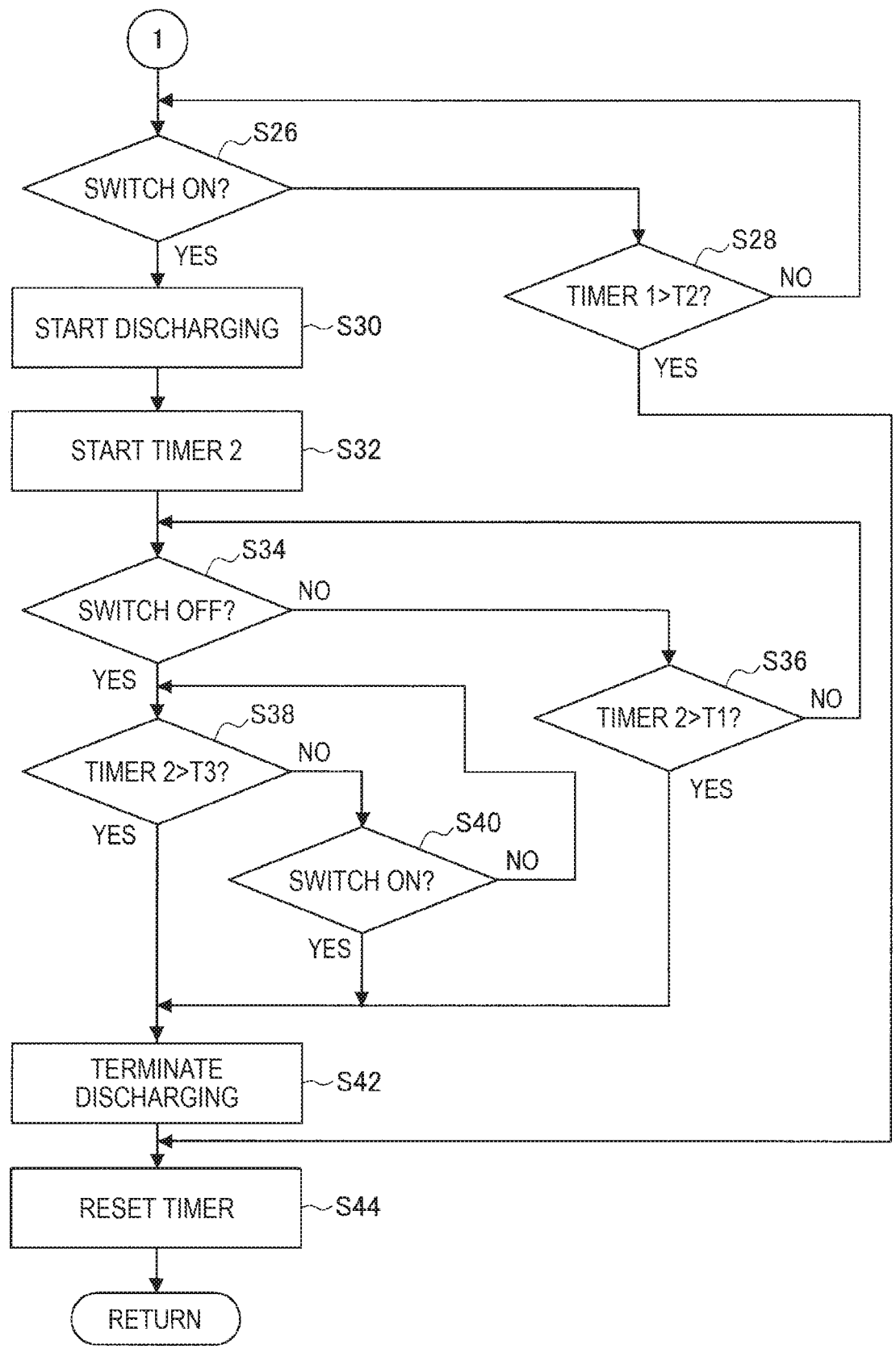
FIG. 12 is a flowchart for describing a flow of the method of controlling the aroma diffusing device according to the embodiment.

Next, a flow of a control method performed by the control circuit of the aroma diffusing device 1 according to the present embodiment will be described in detail. FIG. 11 to FIG. 12 are flowcharts for describing a flow of the method of controlling the aroma diffusing device 1. As described above, in a control system of the aroma diffusing device 1 according to the present embodiment, the state of air supply from the air pump 85 is controlled by the control circuit 102 such as an FPGA, and the flowcharts shown in FIG. 11 to FIG. 12 are explanatory diagrams for easier understanding of transition of discharge state of the aroma diffusing device 1. However, in the case where the air supply state is controlled by a microcomputer such as a CPU, a computer program that may be caused to execute the processing flows shown in FIG. 11 to FIG. 12 may be created in advance for execution by the microcomputer.

First, when the operation button 71 is pressed down so that the switch 110 is switched to on (S10/Yes), the control circuit 102 outputs a chip enable signal to the air pump driving circuit 104 to start air supply from the air pump 85 (S12). In addition, the control circuit 102 starts counting of a timer 1 when air supply is started (S14). Note that, until the switch 110 is switched to on, the control circuit 102 is in a standby state (S10/No).

While the operation button 71 is pressed down and the switch 110 is maintained in the on state (S16/No), for a period until the timer 1 exceeds the first threshold value T1 set in advance, air supply by the air pump 85 is continued (S20/No). On the other hand, while the switch 110 is maintained in the on state (S16/No), in the case where the timer 1 exceeds the first threshold value T1 (S20/Yes), the control circuit 102 stops outputting the chip enable signal with the switch 110 maintained in the on state to terminate air supply from the air pump 85 (S22) (the short-time discharge mode). In such a case, all the timers are reset (S24), and the control circuit 102 returns again to the standby state in step S10.

On the other hand, while air supply by the air pump 85 is continued, before the timer 1 exceeds the first threshold value T1 (S20/No), when the operation button 71 is released so that the switch 110 is switched to off (S16/Yes), the control circuit 102 stops outputting the chip enable signal to terminate air supply from the air pump 85 (S18). In such a case, counting of the timer 1 is continued, and when the timer 1 exceeds the second threshold value T2 set in advance (S28/Yes) without the operation button 71 being pressed down again so that the switch 110 is switched to on (S26/No), all the timers are reset (S44), and the control circuit 102 returns again to the standby state in step S10 (the short-time discharge mode).

On the other hand, before the timer 1 exceeds the second threshold value T2 (S28/No), when the operation button 71 is pressed down again so that the switch 110 is switched to on (S26/Yes), the control circuit 102 outputs a chip enable signal to the air pump driving circuit 104 to start air supply from the air pump 85 (S30). In addition, the control circuit 102 starts counting of a timer 2 when air supply is started (S32).

While the operation button 71 is pressed down and the switch 110 is maintained in the on state (S34/No), for a period until the timer 2 exceeds the first threshold value T1, air supply by the air pump 85 is continued (S36/No). On the other hand, while the switch 110 is maintained in the on state (S34/Yes), in the case where the timer 2 exceeds the first threshold value T1 (S36/Yes), the control circuit 102 stops outputting the chip enable signal with the switch 110 maintained in the on state to terminate air supply from the air pump 85 (S42) (giving a higher priority to the short-time discharge mode). Thereafter, all the timers are reset (S44), and the control circuit 102 returns again to the standby state in step S10.

On the other hand, while air supply by the air pump 85 is continued, before the timer 2 exceeds the first threshold value T1 (S36/No), when the operation button 71 is released so that the switch 110 is switched to off (S34/Yes), the control circuit 102 terminates air supply from the air pump 85 in the following manner. That is, for a while until the timer 2 exceeds the third threshold value T3 after the switch 110 is switched to off (S38/No), in the case where the switch 110 is maintained in the off state, air supply from the air pump 85 is continued (S40/No). In the case where the timer 2 exceeds the third threshold value T3 (S38/Yes) without the switch 110 being switched to on midway (S40/No), the control circuit 102 stops outputting the chip enable signal to terminate air supply from the air pump 85 (the long-time discharge mode). Thereafter, all the timers are reset (S44), and the control circuit 102 returns again to the standby state in step S10.

On the other hand, while air supply by the air pump 85 is continued, until the timer 2 exceeds the third threshold value T3 (S38/No), when the operation button 71 is pressed down again so that the switch 110 is switched to on (S40/Yes), the control circuit 102 immediately stops outputting the chip enable signal to terminate air supply from the air pump 85 (midway cancellation of the long-time discharge mode). Thereafter, all the timers are reset (S44), and the control circuit 102 returns again to the standby state in step S10.

As described above, the control circuit 102 controls the time of air supply from the air pump 85 on the basis of the timing of switching between on and off of the switch 110 by an operation input on the operation button 71. Therefore, a reduction in remaining capacity of the battery 81 is suppressed, and it is possible to allow the perfume cartridge 20 to last a long time. In addition, it is possible for the user to cause the aroma to be discharged at a desired time by operating one operation button 71. Therefore, operability and convenience of the portable aroma diffusing device 1 can be improved.

2. Second Embodiment

Next, an aroma diffusing device and a method of controlling an aroma diffusing device according to a second embodiment of the present disclosure will be described. The overall configuration of the aroma diffusing device according to the present embodiment and the basic configuration of a control system can be similar to the aroma diffusing device 1 and the control system according to the first embodiment. Hereinafter, a specific configuration example of the control system of the aroma diffusing device according to the present embodiment will be mainly described. Note that structural elements common to the aroma diffusing device 1 according to the first embodiment will be described using identical reference characters in the aroma diffusing device 1 according to the first embodiment.

(2-1. Configuration example of control system)

Figure 13:
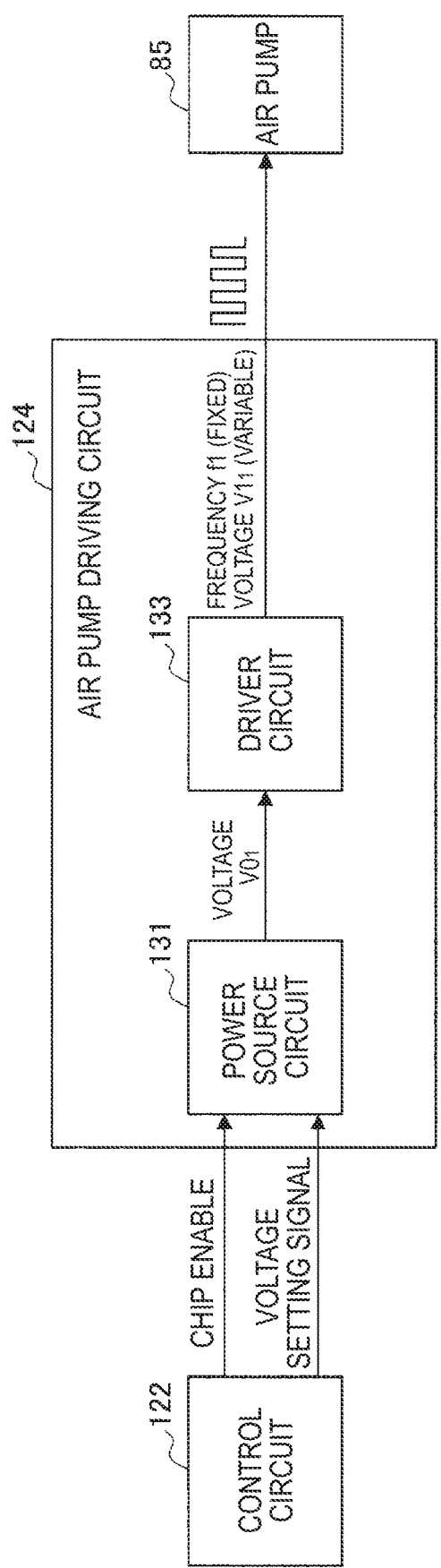
FIG. 13 is a block diagram showing a specific example of a system configuration of an aroma diffusing device according to a first variation.

FIG. 13 is an explanatory diagram specifically showing a configuration of the control system of the aroma diffusing device according to the present embodiment. A control circuit 122 generates a voltage setting signal together with a chip enable signal on the basis of the on/off state of the switch 110 for output to a power source circuit 131 of an air pump driving circuit 124. When the chip enable signal and the voltage setting signal are input, the power source circuit 131 supplies electric power of a voltage $V0_1$ in accordance with the voltage setting signal to a driver circuit 133 for a time set in advance. While electric power is being supplied, the driver circuit 133 outputs a voltage signal of a voltage $V1_1$ generated by amplifying the voltage $V0_1$ to the air pump 85 at the frequency f1 set in advance. While the voltage signal is being input, the air pump 85 supplies a flow rate of air in accordance with the voltage $V1_1$ to the perfume cartridge 20.

Here, in the aroma diffusing device 1 according to the second embodiment, on the basis of the continuous number of operation inputs on one operation button 71, the amount of air supply from the air pump 85 per unit time is controlled, and the discharge amount of aroma is controlled. Accordingly, a plurality of discharge functions are achieved. Specifically, in the aroma diffusing device 1 according to the present embodiment, when the switch 110 is switched to on by an operation input on the operation button 71, the control circuit 122 generates a chip enable signal for a time set in advance. In addition, on the basis of the on/off state of the switch 110 switched by an operation input on the operation button 71, the control circuit 122 controls the voltage $V1_1$ of electric power that drives the air pump 85. Accordingly, the flow rate of air supplied to the perfume cartridge 20 is controlled on the basis of an operation input on the operation button 71. Therefore, in the aroma diffusing device 1 according to the present embodiment, the overall discharge amount can be switched although the time for which the aroma is discharged does not change.

Figure 14:
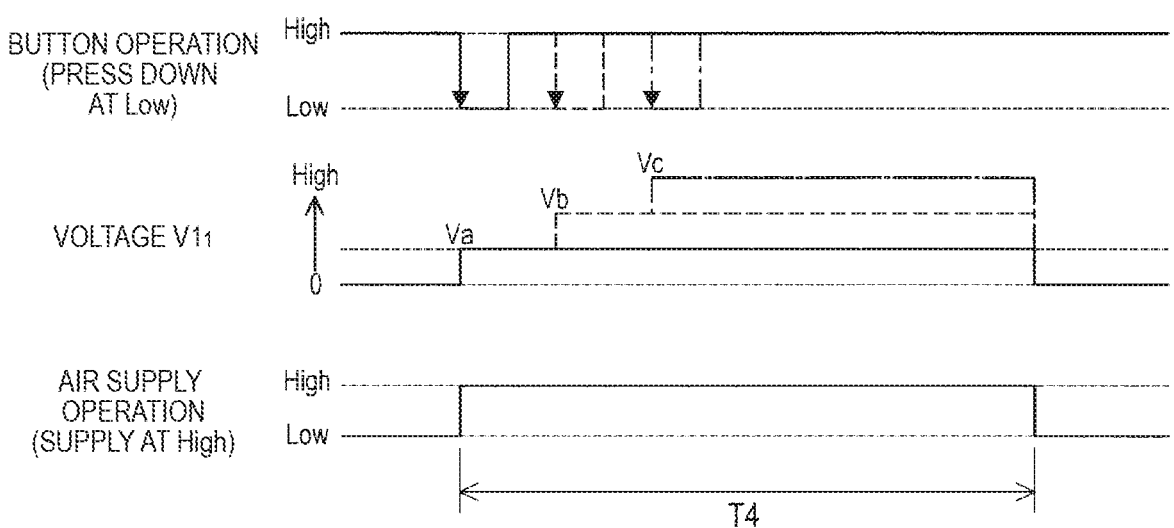
FIG. 14 is an explanatory diagram for describing switching of a supply amount of air.

FIG. 14 is an explanatory diagram for describing control in which the voltage $V1_1$ that drives the air pump 85 is switched in accordance with the pressed state of the operation button 71. FIG. 14 shows the operation state of the operation button 71 (the on/off state of the switch 110), the voltage $V1_1$ supplied to the air pump 85, and the state of an air supply operation performed by the air pump 85. In the operation state of the operation button 71, the "Low" state indicates a state in which the operation button 71 is being pressed down. In addition, in the air supply operation state, the "High" state indicates a state in which air is being supplied.

In the aroma diffusing device 1 according to the present embodiment, the voltage $V1_1$ of electric power supplied to the air pump 85 is set so as to increase step by step in accordance with the number that the operation button 71 is pressed down. Specifically when the first operation input on the operation button 71 is performed so that the switch 110 is switched from off to on, air supply by the air pump 85 is started, and aroma discharge is started. The control circuit 122 starts the timer when the switch 110 is switched to on by the first operation input, and for a while until the timer exceeds a fourth threshold value T4 set in advance, outputs a chip enable signal to the power source circuit 131. The fourth threshold value T4 may be set at an appropriate value. For example, the fourth threshold value T4 may be set at 5 to 20 seconds.

In addition, when the first operation input on the operation button 71 is performed, the control circuit 122 outputs a voltage setting signal by which the voltage $V1_1$ of electric power supplied to the air pump 85 may become a voltage Va to the power source circuit 131. Further, for a while until the timer exceeds the fourth threshold value T4, each time when the second operation input and the third operation input on the operation button 71 are performed, the control circuit 122 outputs a voltage setting signal by which the voltage $V1_1$ of electric power supplied to the air pump 85 may increase step by step to a voltage Vb and a voltage Vc to the power source circuit 131. Accordingly, the amount of air supply supplied to the perfume cartridge 20 per unit time by the air pump 85 is switched.

In the example shown in FIG. 14, the voltage $V1_1$ of electric power supplied to the air pump 85 is variable in three steps, whilst the voltage $V1_1$ may be variable in two steps, or may be variable in four or more steps. In addition, in the example shown in FIG. 14, the control circuit 102 increases the voltage $V1_1$ of electric power supplied to the air pump 85 each time when the continuous number of operation inputs on the operation button 71 increases, whilst the voltage $V1_1$ of electric power supplied to the air pump 85 may be reduced each time when the continuous number of operation inputs on the operation button 71 increases.

In this manner, in the aroma diffusing device 1 according to the present embodiment, the voltage $V1_1$ of electric power supplied to the air pump 85 is changed on the basis of an operation input on one operation button 71, and the amount of air supply per unit time is variable. Therefore, the aroma can be discharged at a desired flow rate even in the case where each user senses a fragrance differently, or even the same user senses a fragrance differently depending on the feeling at the time of use, or the like, for example.

In this manner, in the aroma diffusing device 1 according to the present embodiment, since the discharge amount of aroma per unit time is controlled on the basis of an operation input on one operation button 71, the number of operation buttons is minimized, and the circuit configuration is simplified. Therefore, the aroma diffusing device 1 can be reduced in size, and the manufacturing cost can be suppressed. In addition, in the aroma diffusing device 1 according to the present embodiment, since the discharge amount of aroma per unit time can be switched by an operation input on one operation button 71, user operability and convenience are increased.

Note that, also in the aroma diffusing device 1 according to the present embodiment, in the case where the remaining capacity of the battery 81 has decreased, the light source may be lit up for a predetermined time when the operation button 71 is pressed down so that the switch 110 is switched to on.

(2-2. Variation)

In the aroma diffusing device 1 according to the above-described second embodiment, the discharge amount of aroma per unit time is made variable by changing the voltage $V1_1$ of electric power supplied to the air pump 85, whilst the technique for making the discharge amount of aroma per unit time variable is not limited to such an example. In a variation which will be described below, by changing the frequency of a voltage signal to be supplied to the air pump 85, the discharge amount of aroma per unit time is made variable.

Figure 15:
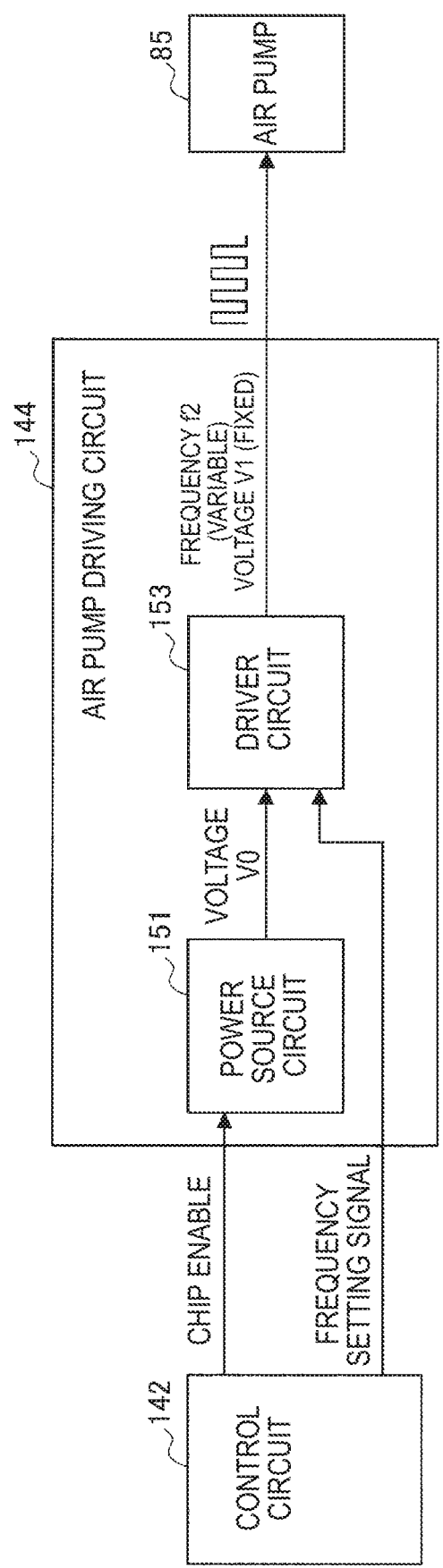
FIG. 15 is a block diagram showing a specific example of a system configuration of an aroma diffusing device according to a second variation.

FIG. 15 is an explanatory diagram specifically showing a configuration of a control system of an aroma diffusing device according to a variation. A control circuit 142 generates a chip enable signal on the basis of the on/off state of the switch 110 for output to a power source circuit 151 of an air pump driving circuit 144, and generates a frequency setting signal for output to a driver circuit 153 of the air pump driving circuit 144. When the chip enable signal is input, the power source circuit 151 supplies electric power of the voltage V0 set in advance to the driver circuit 153 for a time set in advance.

The driver circuit 153 outputs a voltage signal of the voltage V1 generated by amplifying the voltage V0 while electric power is being supplied to the air pump 85 at a frequency f2 set in accordance with the input frequency setting signal. The air pump 85 supplies a flow rate of air in accordance with the voltage $V1_1$ to the perfume cartridge 20 while the voltage signal is being input. The frequency f2 of the voltage signal may be changed by, for example, changing the on/off cycle of a switching element included in the driver circuit 153. Accordingly, the flow rate of air supplied to the perfume cartridge 20 is controlled on the basis of an operation input on the operation button 71. Therefore, in the aroma diffusing device 1 according to a variation, the overall discharge amount can be switched although the time for which the aroma is discharged does not change.

Figure 16:
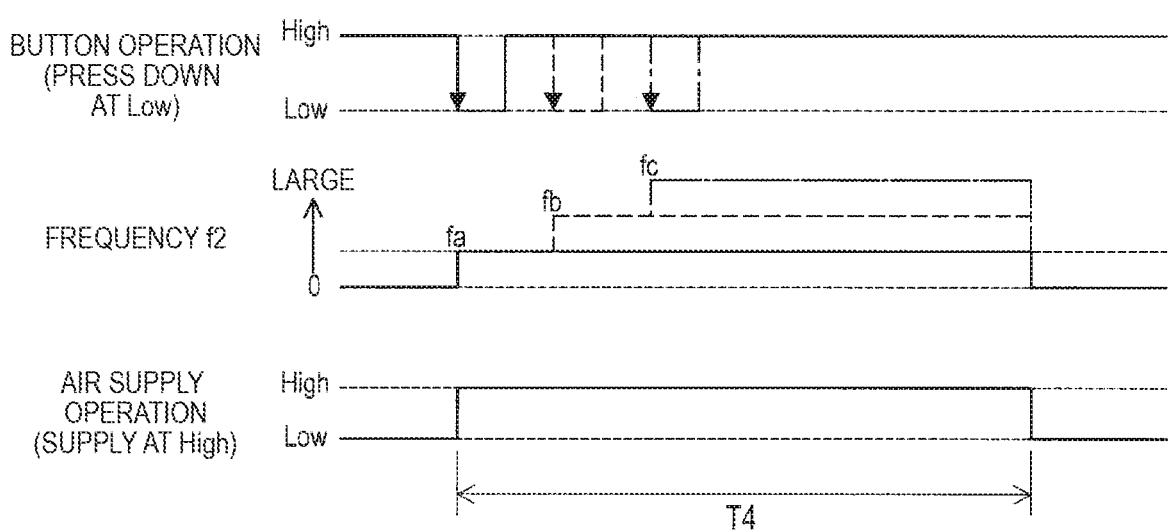
FIG. 16 is an explanatory diagram for describing switching of discharge time.

FIG. 16 is an explanatory diagram for describing control in which the frequency f2 of the voltage signal supplied to the air pump 85 is switched in accordance with the continuous number of operation inputs on the operation button 71. FIG. 16 shows the operation state of the operation button 71 (the on/off state of the switch 110), the frequency f2 of the voltage signal supplied to the air pump 85, and the state of an air supply operation performed by the air pump 85. In the operation state of the operation button 71, the "Low" state indicates a state in which the operation button 71 is being pressed down. In addition, in the air supply operation state, the "High" state indicates a state in which air is being supplied.

In the aroma diffusing device 1 according to the variation, the frequency f2 of the voltage signal supplied to the air pump 85 is set so as to increase step by step in accordance with the number that the operation button 71 is pressed down. Specifically, when the first operation input on the operation button 71 is performed so that the switch 110 is switched from off to on, air supply by the air pump 85 is started, and aroma discharge is started. The control circuit 142 starts the timer when the switch 110 is switched to on by the first operation input, and for a while until the timer exceeds the fourth threshold value T4 set in advance, outputs a chip enable signal to the power source circuit 151.

In addition, when the first operation input on the operation button 71 is performed, the control circuit 122 outputs a frequency setting signal by which the frequency f2 of the voltage signal supplied to the air pump 85 may be a frequency fa to the driver circuit 153. Further, for a while until the timer exceeds the fourth threshold value T4, each time when the second operation input and the third operation input on the operation button 71 are performed, the control circuit 142 outputs a frequency setting signal by which the frequency f2 of the voltage signal supplied to the air pump 85 may be increased step by step to a frequency fb and a frequency fc to the driver circuit 153. Accordingly, the amount of air supply supplied to the perfume cartridge 20 per unit time by the air pump 85 is switched.

In the example shown in FIG. 16, the frequency f2 of the voltage signal supplied to the air pump 85 is variable in three steps, whilst the frequency f2 of the voltage signal may be variable in two steps, or may be variable in four or more steps. In addition, in the example shown in FIG. 16, the control circuit 102 increases the frequency f2 of the voltage signal each time when the continuous number of operation inputs on the operation button 71 increases, whilst the frequency f2 of the voltage signal may be reduced each time when the continuous number of operation inputs on the operation button 71 increases.

In this manner, in the aroma diffusing device 1 according to the variation, the frequency f2 of the voltage signal supplied to the air pump 85 is changed on the basis of an operation input on one operation button 71, and the amount of air supply per unit time is variable. Therefore, also with the aroma diffusing device 1 according to the variation, the aroma can be discharged at a desired flow rate even in the case where each user senses a fragrance differently, or even the same user senses a fragrance differently depending on the feeling at the time of use, or the like, for example.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the method of controlling the air supply state based on on/off of the switch 110 performed by an operation input on the operation button 71 is not limited to the example described in each embodiment described above. For example, the time for which the aroma is discharged may be made variable depending on the continuous number of operation inputs on the operation button 71. For example, the aroma may be discharged for five seconds in the case where the operation button 71 is pressed down once, the aroma may be discharged for ten seconds in the case where the operation button 71 is pressed down twice, and the aroma may be discharged for twenty seconds in the case where the operation button 71 is pressed down three times.

In addition, in each embodiment described above, the aroma diffusing device 1 including one operation button 71 for controlling the state of air supply from the air pump 85 has been described, whilst the aroma diffusing device 1 may include a button or switch for controlling the air supply state other than the operation button 71. For example, a button for lighting up the light source to make such a state display that informs the user of the remaining capacity of the battery 81 may be provided separately from the operation button 71.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An aroma diffusing device including:

a perfume holding part in which a perfume is held;

an air blowing source configured to supply air to the perfume holding part;

an aroma discharge part through which the air having passed through the perfume holding part is discharged;

an operation input part on which an operation input for the air blowing source is performed by a user; and an air blowing source control part configured to control a supply state of the air on the basis of an operation input on the one operation input part.

(2)

The aroma diffusing device according to (1), in which the operation input part switches between on and off of a momentary type switch.

(3)

The aroma diffusing device according to (1) or (2), in which the air blowing source control part controls a supply time of the air.

(4)

The aroma diffusing device according to (3), in which the air blowing source control part varies the supply time of the air on the basis of an interval at which the operation input is performed.

(5)

The aroma diffusing device according to (3) or (4), in which the air blowing source control part starts supply of the air when the operation input is started, and in a case where an elapsed time since the operation input is started is less than or equal to a first threshold value, the air blowing source control part stops supply of the air when the operation input is released.

(6)

The aroma diffusing device according to (5), in which the air blowing source control part stops supply of the air when the elapsed time since the operation input is started exceeds the first threshold value.

(7)

The aroma diffusing device according to any one of (3) to (6), in which in a case where an elapsed time since a first operation input is started until a second operation input is started is less than or equal to a second threshold value, the air blowing source control part stops supply of the air when an elapsed time since the second operation input is started exceeds a third threshold value.

(8)

The aroma diffusing device according to (7), in which the air blowing source control part stops supply of the air when a third operation input is performed until the elapsed time since the second operation input is started exceeds the third threshold value.

(9)

The aroma diffusing device according to (1) or (2), in which the air blowing source control part controls a supply amount of the air for a unit time.

(10)

The aroma diffusing device according to (9), in which the air blowing source control part controls the supply amount of the air for the unit time on the basis of a continuous number of the operation inputs.

(11)

The aroma diffusing device according to (10), in which the air blowing source control part controls the supply amount of the air for the unit time by controlling a voltage to be supplied to the air blowing source on the basis of the continuous number of the operation inputs.

(12)

The aroma diffusing device according to (10), in which the air blowing source control part controls the supply amount of the air for the unit time by controlling a frequency of a voltage signal to be supplied to the air blowing source on the basis of the continuous number of the operation inputs.

(13)

The aroma diffusing device according to any one of (1) to (12), including:

a battery configured to supply electric power to the air blowing source; and a display control part configured to exert control of, when an operation input on the one operation input part is performed, notifying a user of a remaining capacity of the battery.

(14)

The aroma diffusing device according to (13), in which the display control part lights up a light source on the basis of the remaining capacity of the battery.

(15)

The aroma diffusing device according to (14), in which the display control part changes a color of the light source to be lit up on the basis of an operation state of the aroma diffusing device.

(16)

The aroma diffusing device according to any one of (1) to (15), in which the aroma diffusing device is a portable device.

(17)

A method of controlling an aroma diffusing device, the method including:

accepting an operation input on one operation input part made by a user; and activating an air blowing source when the operation input is accepted to pass air through a perfume holding part in which a perfume is held and discharge an aroma, in which a supply state of the air is controlled on the basis of the operation input on the one operation input part.

REFERENCE SIGNS LIST

1 aroma diffusing device
20 perfume holding part (perfume cartridge)
21 air flow path
71 operation button
81 battery
85 air pump
100 circuit board
102 control circuit
104 air pump driving circuit
110 switch 111 power source circuit
113 driver circuit

What is claimed is:

1. An aroma diffusing device comprising:
a perfume holding part in which a perfume is held;
an air blowing source configured to supply air to the perfume holding part;
an aroma discharge part through which the air having passed through the perfume holding part is discharged;
an operation input part; and
an air blowing source control part configured to control a supply state of the air, wherein the supply state of the air is controlled based on an operation input for the air blowing source performed on the operation input part by a user and a supply time of the air is varied based on an interval at which the operation input is performed by the user.

2. The aroma diffusing device according to claim 1, wherein
the operation input part switches between on and off of a momentary type switch.

3. The aroma diffusing device according to claim 1, wherein
the air blowing source control part starts supply of the air when the performance of the operation input begins and, in a case where an elapsed time of the performance of the operation input is less than or equal to a threshold value, the air blowing source control part stops supply of the air when the performance of the operation input ends.

4. The aroma diffusing device according to claim 3, wherein, in a case where the elapsed time of the performance of the operation input is greater than the threshold value, the air blowing source control part stops supply of the air when the elapsed time exceeds the threshold value.

5. The aroma diffusing device according to claim 1, wherein, in a case where an elapsed time between an initiation of the performance of the operation input and an initiation of a performance of a second operation input is less than or equal to a first threshold value, the air blowing source control part stops supply of the air when an elapsed time since the initiation of the performance of the second operation input exceeds a second threshold value.

6. The aroma diffusing device according to claim 5, wherein, in a case where a third operation input is performed prior to the elapsed time since the initiation of the performance of the second operation input exceeding the second threshold value, the air blowing source control part stops supply of the air when the third operation input ceases to be performed.

7. The aroma diffusing device according to claim 1, wherein the air blowing source control part controls a supply amount of the air for the supply time.

8. The aroma diffusing device according to claim 7, wherein the air blowing source control part controls the supply amount of the air for the supply time on a basis of a number of times the operation input is performed.

9. The aroma diffusing device according to claim 8, wherein the air blowing source control part controls the supply amount of the air for the supply time by controlling a voltage supplied to the air blowing source on a basis of the number of times the operation input is performed.

10. The aroma diffusing device according to claim 8, wherein the air blowing source control part controls the supply amount of the air for the supply time by controlling a frequency of a voltage signal supplied to the air blowing source on a basis of the number of times the operation input is performed.

11. The aroma diffusing device according to claim 1, further comprising:
a battery configured to supply electric power to the air blowing source; and
a display control part configured to, when the operation input is performed, notify a user of a remaining capacity of the battery.

12. The aroma diffusing device according to claim 11, wherein the display control part lights up a light source on a basis of the remaining capacity of the battery.

13. The aroma diffusing device according to claim 12, wherein the display control part changes a color of the light source on a basis of an operation state of the aroma diffusing device.

14. The aroma diffusing device according to claim 1, wherein the aroma diffusing device is a portable device.

15. A method of controlling an aroma diffusing device, the method comprising:
detecting performance by a user of an operation input for an air blowing source on an operation input part of the aroma diffusing device, wherein the air blowing source is configured to supply air to a perfume holding part of the aroma diffusing device in which a perfume is held;
controlling a supply state of the air, by an air blowing source control part, based on the operation input for the air blowing source performed on the operation part by the user; and
varying a supply time of the air based on an interval at which the operation input is performed by the user.

16. The method of claim 15, wherein the operation input part switches between on and off of a momentary type switch.

17. The method of claim 15, wherein the air blowing source control part starts supply of the air when the performance of the operation input begins and, in a case where an elapsed time of the performance of the operation input is less than or equal to a threshold value, the air blowing source control part stops supply of the air when the performance of the operation input ends.

18. The method of claim 17, wherein, in a case where the elapsed time of the performance of the operation input is greater than the threshold value, the air blowing source control part stops supply of the air when the elapsed time exceeds the threshold value.

19. The method of claim 15, wherein, in a case where an elapsed time between an initiation of the performance of the operation input and an initiation of a performance of a second operation input is less than or equal to a first threshold value, the air blowing source control part stops supply of the air when an elapsed time since the initiation of the performance of the second operation input exceeds a second threshold value.

20. The method of claim 15, wherein, in a case where a third operation input is performed prior to the elapsed time since the initiation of the performance of the second operation input exceeding the second threshold value, the air blowing source control part stops supply of the air when the third operation input ceases to be performed.

* * * * *